(12) United States Patent
Bessho

(10) Patent No.: US 12,393,015 B2
(45) Date of Patent: Aug. 19, 2025

(54) ENDOSCOPE

(71) Applicant: HOYA CORPORATION, Tokyo (JP)

(72) Inventor: Hisanori Bessho, Tokyo (JP)

(73) Assignee: HOYA CORPORATION, Tokyo (JP)

( * ) Notice: Subject to any disclaimer, the term of this patent is extended or adjusted under 35 U.S.C. 154(b) by 0 days.

(21) Appl. No.: 18/286,258

(22) PCT Filed: Jul. 7, 2022

(86) PCT No.: PCT/JP2022/026906
§ 371 (c)(1),
(2) Date: Oct. 10, 2023

(87) PCT Pub. No.: WO2023/013356
PCT Pub. Date: Feb. 9, 2023

(65) Prior Publication Data
US 2024/0192480 A1 Jun. 13, 2024

(30) Foreign Application Priority Data
Aug. 2, 2021 (JP) .................. 2021-126742

(51) Int. Cl.
*G02B 23/24* (2006.01)
*H05K 7/20* (2006.01)

(52) U.S. Cl.
CPC ..... *G02B 23/2484* (2013.01); *H05K 7/20409* (2013.01); *H05K 7/20463* (2013.01); *H05K 7/20481* (2013.01)

(58) Field of Classification Search
CPC ........... G02B 23/2484; H05K 7/20409; H05K 7/20463; H05K 7/20481

USPC .......................................................... 348/65
See application file for complete search history.

(56) References Cited

U.S. PATENT DOCUMENTS

| 2011/0094827 | A1 | 4/2011 | Takahashi et al. |
| 2017/0333125 | A1 | 11/2017 | Lepak et al. |
| 2019/0371833 | A1* | 12/2019 | Hogyoku ............... H04N 23/00 |
| 2022/0341790 | A1 | 10/2022 | Toda et al. |

FOREIGN PATENT DOCUMENTS

| DE | 102006032079 A1 | 1/2007 |
| EP | 0978251 A1 | 2/2000 |
| JP | 2004-8638 A | 1/2004 |

(Continued)

OTHER PUBLICATIONS

International Search Report issued in WIPO Patent Application No. PCT/JP2022/026906, dated Aug. 16, 2022, along with an English translation thereof.

(Continued)

*Primary Examiner* — Jeffery A Williams
(74) *Attorney, Agent, or Firm* — GREENBLUM & BERNSTEIN, P.L.C.

(57) ABSTRACT

To provide an endoscope capable of appropriately dissipating heat of a heat generating portion with a simpler configuration.
In an endoscope including an image sensor that generates heat during operation, and a shield pipe and a mold resin portion that are integrated with the image sensor and dissipate heat transferred from the image sensor in a case where the image sensor generates heat, the mold resin portion has a linear expansion coefficient larger than those of the image sensor and the shield pipe.

9 Claims, 4 Drawing Sheets

(56) References Cited

FOREIGN PATENT DOCUMENTS

| | | |
|---|---|---|
| JP | 2006-94955 A | 4/2006 |
| JP | 2007-156079 A | 6/2007 |
| JP | 2011-50545 A | 3/2011 |
| JP | 2011-200398 A | 10/2011 |
| JP | 5189209 B2 | 4/2013 |
| JP | 2015-217162 A | 12/2015 |
| JP | 2018-535739 A | 12/2018 |
| JP | 2021-39055 A | 3/2021 |
| WO | 2010/004996 A1 | 1/2010 |

OTHER PUBLICATIONS

Notice of Reasons for Refusal issued in Japanese Patent Application No. 2021-126742 dated Oct. 8, 2024, together with an English translation.
Extended European Search Report issued in European Application No. 22 852 782.6, issued May 27, 2025.

\* cited by examiner

ENDOSCOPE

TECHNICAL FIELD

The present invention relates to an endoscope.

The present application claims priority based on Japanese Patent Application No. 2021-126742 filed on Aug. 2, 2021, the entire contents of which are incorporated herein by reference.

BACKGROUND ART

In recent years, with an increasing need for image quality enhancement in an endoscope, an increase in the number of pixels of an image sensor has been advanced. However, since power consumption increases due to the increase in the number of pixels of the image sensor, the amount of heat generated from the image sensor increases accordingly. Therefore, it is necessary to devise a method of dissipating heat of the image sensor.

Patent Literature 1 discloses an endoscope in which a cooling device is provided between an image sensor and a wiring board, and heat generated from the image sensor can be effectively dissipated.

Patent Literature 2 discloses an endoscope that efficiently dissipates heat from a circuit board by filling two different types of resins to solidify an image sensor and the circuit board.

Patent Literature 3 discloses an endoscope including a heat dissipation member that is attached to a distal end portion and has a plurality of fins for dissipating heat of the distal end portion.

CITATION LIST

Patent Literature

Patent Literature 1: JP 2015-217162 A
Patent Literature 2: JP 2011-200398 A
Patent Literature 3: JP 2007-156079 A

SUMMARY OF INVENTION

Technical Problem

However, a cooling device is provided in the endoscope of Patent Literature 1, two different types of resins are used in the endoscope of Patent Literature 2, and a heat dissipation member is provided at the distal end portion of the endoscope in Patent Literature 3. In any of the endoscopes of Patent Literatures 1 to 3, a separate member is required for heat dissipation, and thus, the endoscopes have a complicated configuration.

The present invention has been made in view of such circumstances, and an object thereof is to provide an endoscope capable of appropriately dissipating heat of a heat generating portion with a simple configuration without requiring a separate member for head dissipation.

Solution to Problem

An endoscope according to the present invention is an endoscope including a heat generating portion that generates heat during operation and a heat dissipation member that dissipates heat transferred from the heat generating portion. The heat dissipation member includes a first heat dissipation member that covers the heat generating portion and a second heat dissipation member with a cylindrical shape in which the first heat dissipation member is internally fitted, and the first heat dissipation member has a linear expansion coefficient larger than linear expansion coefficients of the heat generating portion and the second heat dissipation member.

According to the present invention, the linear expansion coefficient of the first heat dissipation member that covers the heat generating portion is larger than that of the heat generating portion, and the linear expansion coefficient of the first heat dissipation member is larger than that of the second heat dissipation member with a cylindrical shape in which the first heat dissipation member is internally fitted. Therefore, the thermal expansion amount of the first heat dissipation member is larger than those of the heat generating portion and the second heat dissipation member. Therefore, in a case where the heat generating portion generates heat, the first heat dissipation member can be brought into close contact with the heat generating portion and the second heat dissipation member, and heat of the heat generating portion is quickly transferred to the second heat dissipation member on the outer side via the first heat dissipation member.

In the endoscope according to the present invention, an intervention member formed in a sheet shape is disposed between the first heat dissipation member and the second heat dissipation member, and a linear expansion coefficient of the intervention member is larger than linear expansion coefficients of the heat generating portion and the heat dissipation member.

In the present invention, since the linear expansion coefficient of the intervention member is larger than the linear expansion coefficients of the heat generating portion and the heat dissipation member, the thermal expansion amount of the intervention member is larger than that of the heat dissipation member. Therefore, in a case where the heat generating portion generates heat, the first heat dissipation member and the second heat dissipation member can be brought into close contact with each other via the intervention member, and heat of the heat generating portion is quickly transferred to the second heat dissipation member outside the first heat dissipation member.

The endoscope according to the present invention further includes an outer member in which the second heat dissipation member is internally fitted, and the outer member has a linear expansion coefficient larger than a linear expansion coefficient of the second heat dissipation member.

In the present invention, since the linear expansion coefficient of the outer member is larger than the linear expansion coefficient of the second heat dissipation member, the thermal expansion amount of the outer member is larger than that of the second heat dissipation member. Therefore, in a case where the heat generating portion generates heat, the outer member and the second heat dissipation member do not come into close contact with each other, and heat of the heat generating portion is less likely to be transferred to the outer member via the second heat dissipation member. As a result, it is possible to prevent the skin of the patient from coming into contact with the outer member and burning.

In the endoscope according to the present invention, the outer member includes a first outer member exposed to outside and a second outer member not exposed, and the first outer member has a thermal conductivity lower than a thermal conductivity of the second outer member.

According to the present invention, since the first outer member that is exposed to the outside and possibly comes into contact with the skin of the patient has a thermal conductivity lower than that of the second outer member, it is possible to prevent the skin of the patient from coming into contact with the first outer member and burning even in a case where heat of the heat generating portion is transferred to the first outer member via the second heat dissipation member.

The endoscope according to the present invention further includes an exterior member with a circular tube shape in which the second outer member with a cylindrical shape is internally fitted, and a thermal conductivity of the exterior member is equal to or less than 0.1 W/(m·K).

According to the present invention, since the thermal conductivity of the exterior member that possibly comes into contact with the skin of the patient is low such as 0.1 W/(m·K) or less, it is possible to prevent the skin of the patient from coming into contact with the exterior member and burning even in a case where heat of the heat generating portion is transferred to the second outer member via the second heat dissipation member.

In the endoscope according to the present invention, a thermal conductivity of the exterior member is equal to or less than 0.05 W/(m·K).

According to the present invention, since the thermal conductivity of the exterior member that possibly comes into contact with the skin of the patient is low such as 0.05 W/(m·K) or less, it is possible to more reliably prevent the skin of the patient from coming into contact with the exterior member and burning.

In the endoscope according to the present invention, the first heat dissipation member includes epoxy, and the second heat dissipation member includes nickel.

According to the present invention, the first heat dissipation member includes epoxy, and the second heat dissipation member includes nickel.

In the endoscope according to the present invention, a compression rate of the second heat dissipation member is equal to or more than 20%.

According to the present invention, the compression rate of the second heat dissipation member in a case where heat is generated in the heat generating portion is equal to or more than 20% with respect to a case where heat is not generated in the heat generating portion.

In the endoscope according to the present invention, a compression rate of the intervention member is equal to or more than 20%.

According to the present invention, the compression rate of the intervention member in a case where heat is generated in the heat generating portion is equal to or more than 20% with respect to a case where heat is not generated in the heat generating portion.

Advantageous Effects of Invention

According to the present invention, heat of the heat generating portion can be appropriately dissipated with a simpler configuration.

DESCRIPTION OF EMBODIMENTS

Hereinafter, an endoscope according to an embodiment of the present invention will be described in detail with reference to the drawings.

Figure 1:
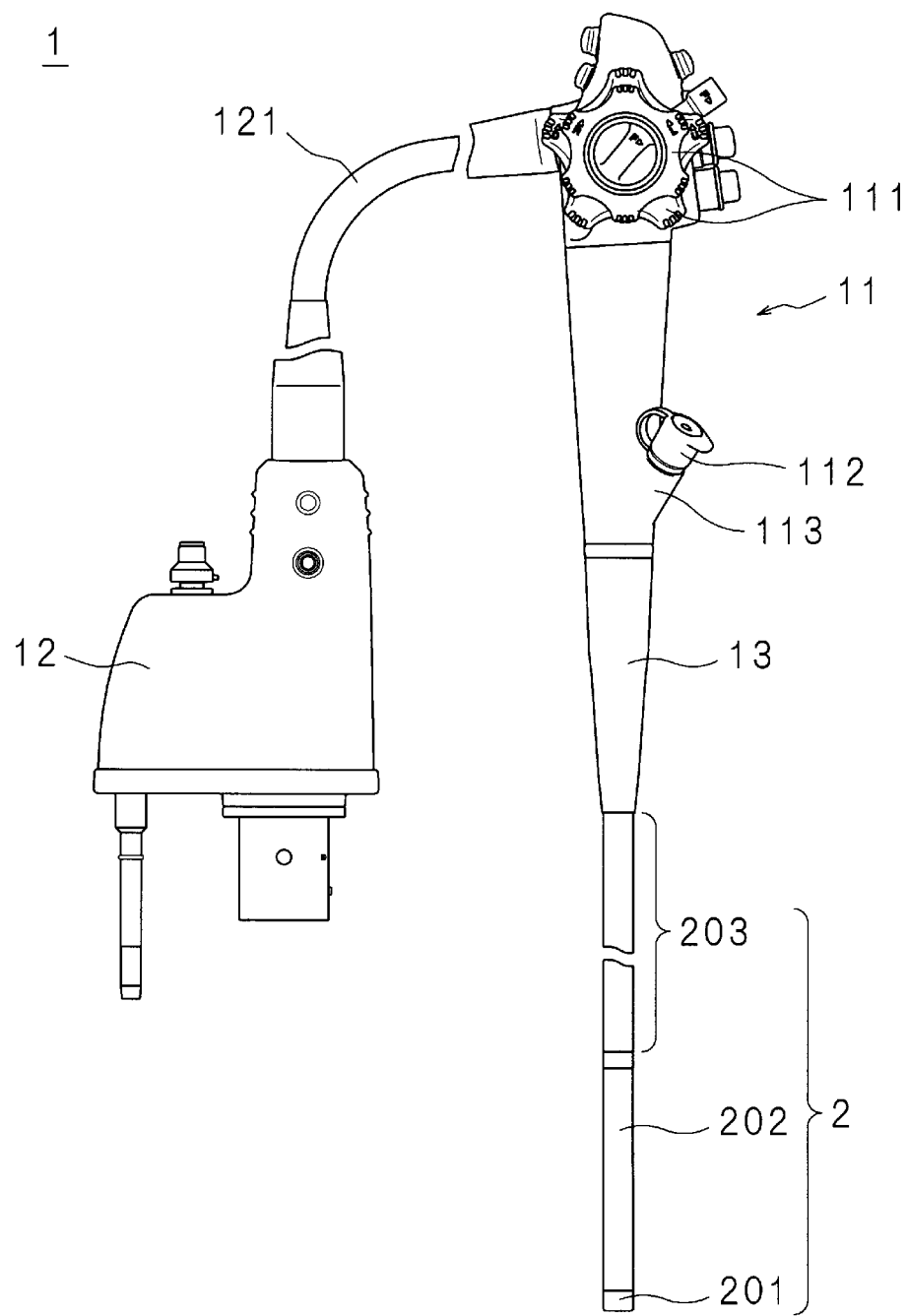
FIG. 1 is an external view of an endoscope according to an embodiment of the present invention.

FIG. 1 is an external view of the endoscope according to the embodiment of the present invention.

An endoscope 1 is a flexible scope for the upper gastrointestinal tract or the lower gastrointestinal tract. The endoscope 1 includes an operation unit 11, a connector unit 12, and an insertion portion 2. A bend preventing portion 13 is provided between the insertion portion 2 and the operation unit 11.

The operation unit 11 has a tubular shape, and includes an operation knob 111 at one end portion and a channel inlet 113 at the other end portion. The channel inlet 113 includes a forceps plug 112.

The connector unit 12 is connected to the operation unit 11 via a universal cord 121. The connector unit 12 is connected to a power supply device, a display device, and the like (not illustrated). A power line and a signal line (not illustrated) are wired from the connector unit 12 to the insertion portion 2 through the universal cord 121, the operation unit 11, the bend preventing portion 13, and the insertion portion 2.

The bend preventing portion 13 communicates with the other end portion of the operation unit 11 and has a cylindrical shape whose diameter decreases toward the side of the insertion portion 2.

The insertion portion 2 has an elongated tubular shape, and includes a distal end portion 201, a bending portion 202, and a soft portion 203 in this order from the distal end side. The distal end portion 201 is the shortest and hardest. The bending portion 202 has flexibility. The soft portion 203 is the longest and flexible.

Figure 2:
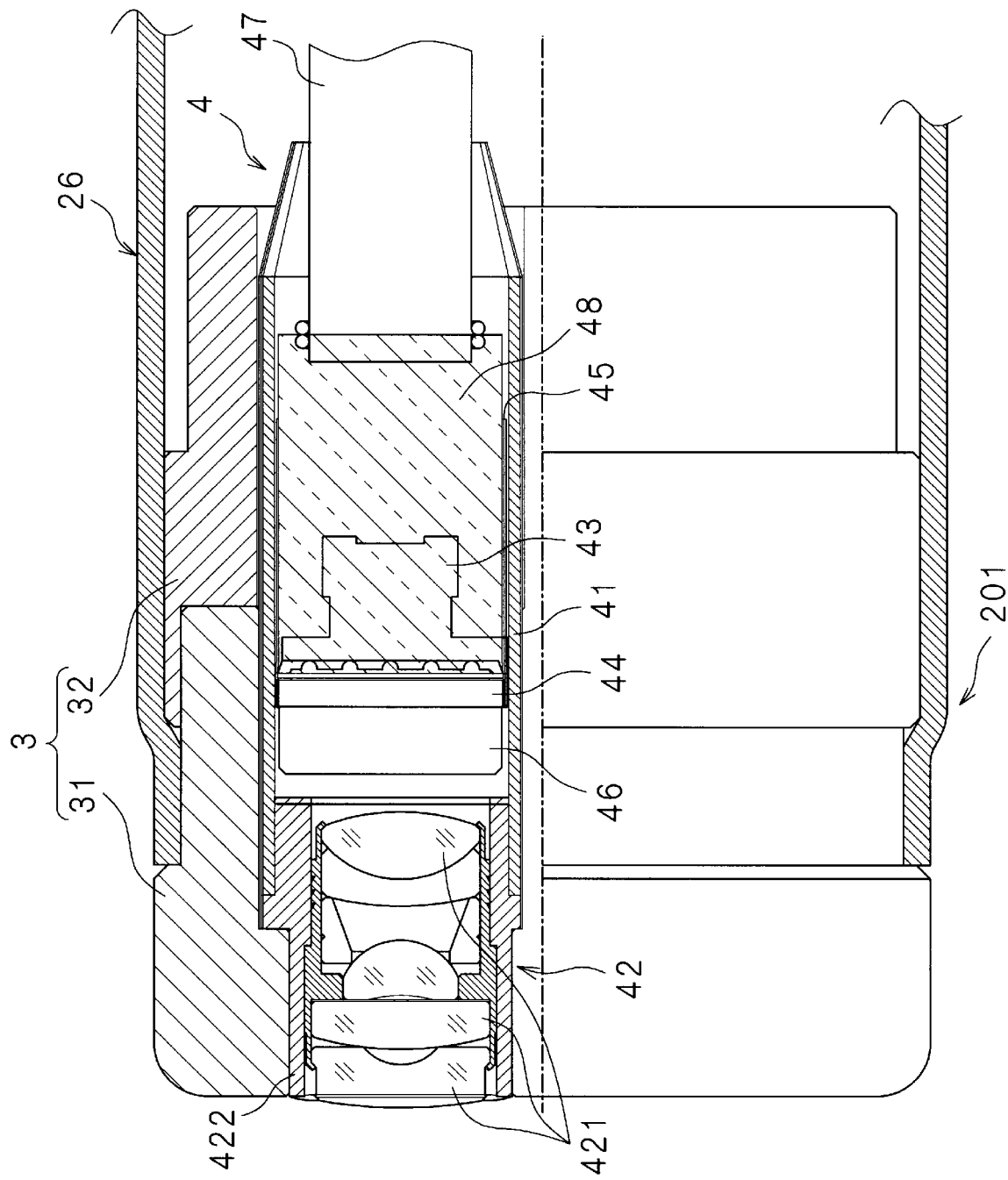
FIG. 2 is a cross-sectional view of an insertion portion of the endoscope according to the present embodiment.

FIG. 2 is a cross-sectional view of the insertion portion 2 of the endoscope 1 according to the present embodiment. FIG. 2 illustrates the distal end portion 201 of the insertion portion 2. The distal end portion 201 includes an imaging assembly 4 along the axial length direction of the distal end portion, and the imaging assembly 4 is surrounded by an outer member 3.

Figure 3:
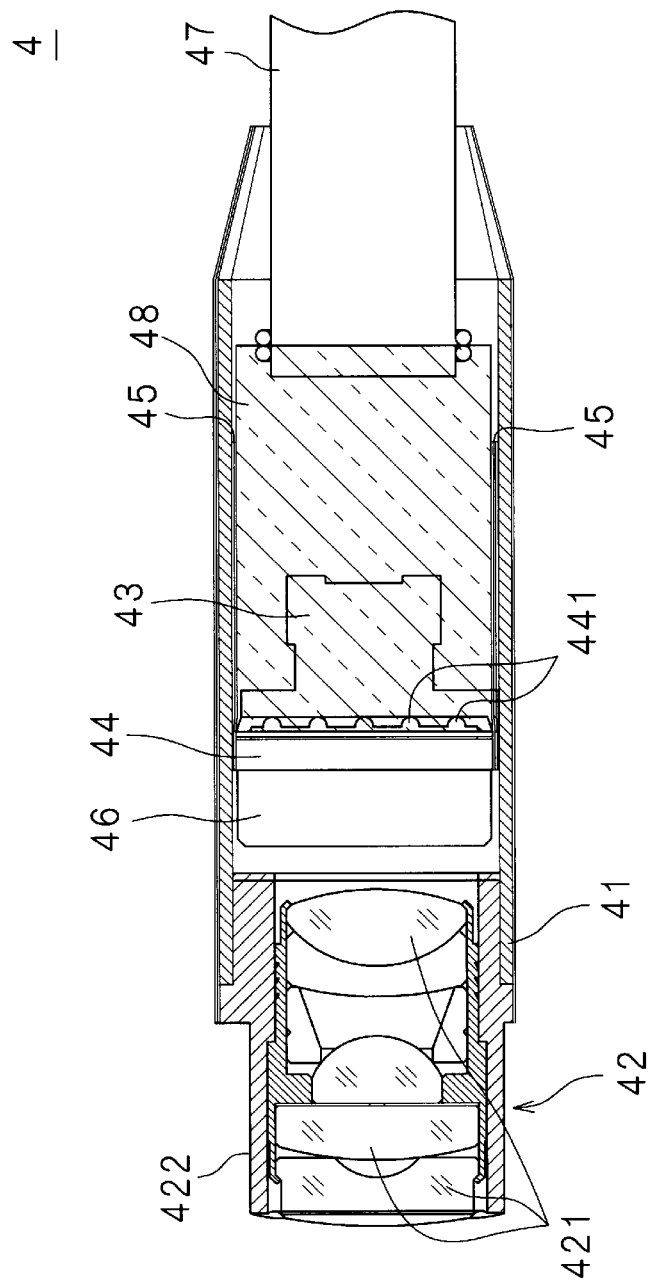
FIG. 3 is an enlarged cross-sectional view illustrating the imaging assembly illustrated in FIG. 2 in an enlarged manner.

FIG. 3 is an enlarged cross-sectional view illustrating the imaging assembly 4 illustrated in FIG. 2 in an enlarged manner.

The imaging assembly 4 includes an image sensor 44 (heat generating portion), a cylindrical shield pipe 41 (second heat dissipation member) that houses the image sensor 44 and has a rectangular cross-sectional view, and a mold resin portion 48 (first heat dissipation member) that is formed in the shield pipe 41 and integrates the image sensor 44 and the shield pipe 41. Heat generated by the image sensor 44 is absorbed and dissipated by the shield pipe 41 or the mold resin portion 48. That is, the shield pipe 41 and the mold resin portion 48 are heat dissipation members.

The shield pipe 41 is made of, for example, nickel. An objective lens unit 42 is provided at one end of the shield pipe 41, and a cable 47 is inserted into the shield pipe 41 from the other end of the shield pipe 41.

The image sensor 44 is, for example, a complementary metal oxide semiconductor (CMOS) image sensor or a charge coupled device (CCD). The image sensor 44 has a plate shape. The image sensor 44 is internally fitted in the shield pipe 41, and its side surface is in contact with the inner surface of the shield pipe 41.

In the shield pipe 41, a cover lens 46 is provided on the light receiving surface side of the image sensor 44. The cover lens 46 includes a cover glass, a color filter, a microlens, and the like. That is, the cover lens 46 covers the light receiving surface of the image sensor 44.

The image sensor 44 converts an optical image formed on the light receiving surface into an electrical signal and outputs the electrical signal to the display device. In the shield pipe 41, a plurality of electrodes 441 for inputting and outputting electric signals are provided in a projecting manner on a surface of the image sensor 44 opposite to the light receiving surface. In addition, a mounting substrate 43 is provided adjacent to the electrodes 441. That is, the image sensor 44 is connected to the mounting substrate 43 via the electrodes 441.

Moreover, in the shield pipe 41, a driver IC (not illustrated) or the like is mounted on the mounting substrate 43, and the mounting substrate 43 and the cable 47 are connected via an electric wire. The driver IC drives the image sensor 44.

The driver IC is then electrically connected to one end portion of the cable 47. The cable 47 has a structure in which the power line and the signal line mentioned above are covered with a sheath, and has pliability. The cable 47 is used for supplying power from the power supply device mentioned above to the image sensor 44, and outputting a signal from the image sensor 44 to the display device. The cable 47 is connected to a flexible printed circuit board.

Furthermore, in the shield pipe 41, a mold resin is filled from the image sensor 44 to one end portion of the cable 47 to form the mold resin portion 48. More specifically, the mold resin portion 48 is formed so as to cover the side of the electrode 441 of the image sensor 44 and the mounting substrate 43. In FIGS. 2 and 3, the mold resin portion 48 is indicated by hatching.

The mold resin portion 48 is, for example, a highly thermally conductive resin in which a thermally conductive filler is blended, and has high insulating properties. In addition, the thermal conductivity of the mold resin portion 48 is, for example, 2.4 W/(m·K). The driver IC, the flexible printed circuit board, and the connection portion of the cable 47 with the flexible printed circuit board are molded by the mold resin portion 48, and the occurrence of electrical disconnection is prevented. In addition, the mold resin portion 48 absorbs heat generated from the image sensor 44, the driver IC, and the flexible printed circuit board and transmits the heat to the shield pipe 41.

That is, the mold resin portion 48 has a substantially rectangular parallelepiped shape and is internally fitted in the shield pipe 41. The mold resin portion 48 is made of, for example, epoxy and has a linear expansion coefficient larger than that of the shield pipe 41. The linear expansion coefficient of the mold resin portion 48 is $55.5 \times 10^{-6}/°$ C., which is larger than that of the shield pipe 41 ($15.5 \times 10^{-6}/°$ C.).

Moreover, the mold resin portion 48 has a linear expansion coefficient larger than those of the image sensor 44 and the shield pipe 41. The linear expansion coefficient of the image sensor 44 is about $3.43 \times 10^{-6}/°$ C. because the main structure of the image sensor 44 is Si single crystal. On the other hand, the mold resin portion 48 is made of resin as described above, and has a linear expansion coefficient of $55.5 \times 10^{-6}/°$ C. The shield pipe 41 is made of nickel as described above, and has a linear expansion coefficient of $15.5 \times 10^{-6}/°$ C.

A sheet-like intervention member 45 is disposed between the image sensor 44 and the mold resin portion 48, and the shield pipe 41 for airtightness, insulation, and the like. That is, the intervention member 45 is formed in a sheet shape and surrounds the image sensor 44 and the mold resin portion 48. The intervention member 45 is made of, for example, silicon-based rubber, and an adhesive may be applied to the principal surface of the intervention member 45.

The linear expansion coefficient of the intervention member 45 is 2.5 to $4.0 \times 10^{-4}/°$ C., which is larger than the linear expansion coefficients of the image sensor 44 ($3.43 \times 10^{-6}/°$ C.), the mold resin portion 48 ($55.5 \times 10^{-6}/°$ C.), and the shield pipe 41 ($15.5 \times 10^{-6}/°$ C.).

As described above, since the linear expansion coefficient of the intervention member 45 is larger than the linear expansion coefficients of the mold resin portion 48 and the shield pipe 41, in a case where thermal expansion occurs due to heat generation of the image sensor 44, the mold resin portion 48 and the shield pipe 41 can be brought into close contact with each other via the intervention member 45.

In addition, the intervention member 45 has a compression rate of 20% or more by the shield pipe 41 and the mold resin portion 48 in a high temperature environment of 70 to 80° C. Here, the compression rate is obtained by the following Formula 1, $$\{(T1-T2)/T1\} \times 100 \quad \text{(Formula 1)}$$

where T1 is a thickness before the intervention member 45 is interposed between the shield pipe 41 and the mold resin portion 48, and T2 is a thickness in the high temperature environment when the intervention member 45 is interposed between the shield pipe 41 and the mold resin portion 48.

Figure 4:
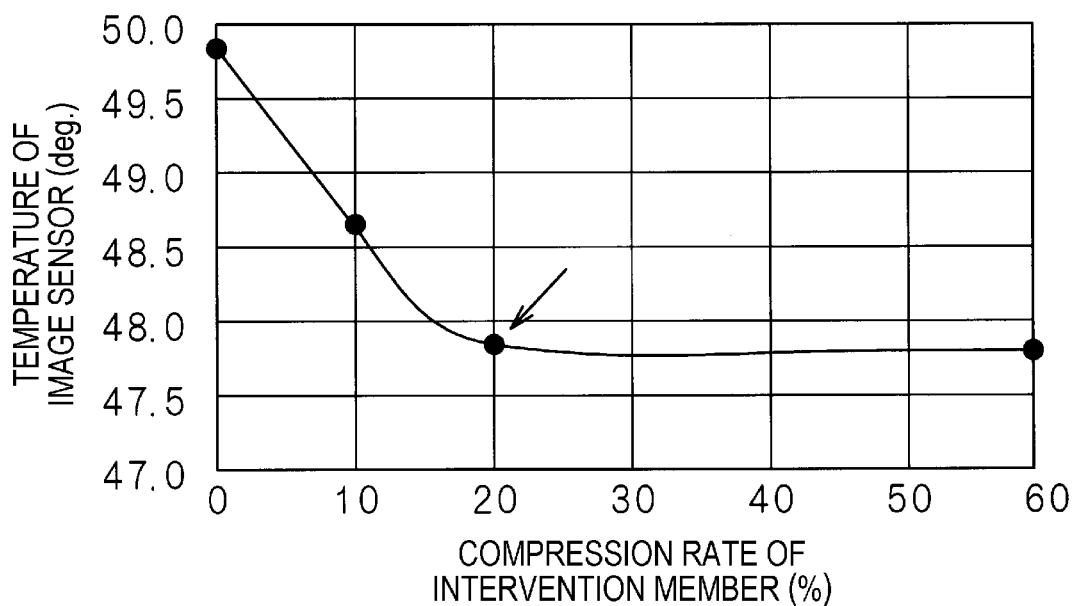
FIG. 4 is a graph showing a relationship between a temperature of an image sensor and a compression rate of an intervention member in the endoscope according to the present embodiment.

FIG. 4 is a graph showing a relationship between a temperature of the image sensor 44 and a compression rate of the intervention member 45 in the endoscope 1 according to the present embodiment. In FIG. 4, the horizontal axis represents the compression rate (%) of the intervention member 45, and the vertical axis represents the temperature of the image sensor 44.

As can be seen from FIG. 4, the temperature of the image sensor 44 decreases as the compression rate of the intervention member 45 increases. In other words, it can be said that a larger amount of heat of the image sensor 44 is dissipated as the compression rate of the intervention member 45 increases. In addition, in a case where the compression rate of the intervention member 45 exceeds 20% (see the arrow in FIG. 4), the amount of decrease in the temperature of the image sensor 44 hardly changes.

As described above, since the linear expansion coefficient of the intervention member 45 is larger than the linear expansion coefficients of the mold resin portion 48 and the shield pipe 41, and the compression rate of the intervention member 45 is equal to or more than 20%, heat generated from the image sensor 44 is quickly transferred to the shield pipe 41 via the intervention member 45, and is effectively dissipated.

Note that the intervention member 45 is not limited to the silicon-based rubber, and may be made of polyimide-based materials, polyester-based materials, silicone-based sheets, urethane-based materials, acryl-based materials, hot-melt-based materials, or the like.

The objective lens unit 42 includes a plurality of imaging lenses 421, 421, . . . and a lens holding tube 422.

The lens holding tube 422 has a square tube shape and has an inner peripheral surface with a circular cross-section. In the lens holding tube 422, the thickness of a half close to the shield pipe 41 is thicker than the thickness of the remaining half in the axial length direction. Furthermore, in the lens holding tube 422, a step is formed along a circumferential direction on the outer peripheral surface of one end portion on the side of the shield pipe 41, and a reduced diameter portion whose outer diameter is reduced is provided. The outer diameter of the reduced diameter portion is slightly smaller than the inner diameter of the one end portion of the shield pipe 41, and the one end portion of the shield pipe 41 is externally fitted to the one end portion of the lens holding tube 422.

The plurality of imaging lenses 421, 421, . . . are fitted into the lens holding tube 422. The plurality of imaging lenses 421, 421, . . . are arranged on the axial center of the lens holding tube 422.

As illustrated in FIG. 2, the imaging assembly 4 is internally fitted in the outer member 3.

The outer member 3 includes a distal end cylindrical portion 31 (first outer member) and a cylindrical body 32 (second outer member). The distal end cylindrical portion 31 has a bottomed cylindrical shape, and the cylindrical body 32 has a cylindrical shape. The distal end of the lens holding tube 422 is exposed to the outside through a through-hole formed in the bottom of the distal end cylindrical portion 31.

One end portion of the distal end cylindrical portion 31 is fitted to one end portion of the cylindrical body 32 on the same axial center. Specifically, the cylindrical body 32 includes a step formed along the circumferential direction on the inner peripheral surface of the one end portion, and thus includes an enlarged diameter portion in which the inner diameter is enlarged. The inner diameter of the enlarged diameter portion is slightly larger than the outer diameter of the one end portion of the distal end cylindrical portion 31, and the one end portion of the distal end cylindrical portion 31 is internally fitted in the one end portion of the cylindrical body 32.

The distal end cylindrical portion 31 is made of a resin such as m-PPE (NORYL, IUPIACE), PPSU (Radel), POM, PPE, PC, PP, ABS, or PMMA. The one end portion of the distal end cylindrical portion 31 is internally fitted in a cover tube 26 (exterior member) to be described later, and the other end portion on the distal end side is exposed to the outside.

In addition, a plurality of through-holes penetrating the bottom are formed in the bottom of the distal end cylindrical portion 31, and one end portion of the imaging assembly 4 is exposed to the outside through one through-hole as described above. In addition, one end of a channel tube (not illustrated) is open through another through-hole. The channel tube extends over the entire length of the insertion portion 2, and the other end thereof is connected to the channel inlet 113 of the operation unit 11.

The cylindrical body 32 is made of metal such as SUS, Cu, brass, Al, Ti, or Fe. The cylindrical body 32 is internally fitted in the cover tube 26 and is not exposed to the outside.

The thermal conductivity of the distal end cylindrical portion 31 is lower than that of the cylindrical body 32. For example, the thermal conductivity of the distal end cylindrical portion 31 is equal to or less than 0.5 W/(m·K), and the thermal conductivity of the cylindrical body 32 is equal to or more than 20 W/(m·K).

Furthermore, it is configured in the endoscope 1 according to the present embodiment that the linear expansion coefficients of the distal end cylindrical portion 31 and the cylindrical body 32 are larger than that of the shield pipe 41.

That is, the distal end cylindrical portion 31 is made of resin and has a linear expansion coefficient larger than that of the shield pipe 41 made of a metal-based material. In the cylindrical body 32, a material with a linear expansion coefficient larger than that of the shield pipe 41 is selected from the materials listed above.

Therefore, in a case where heat is generated from the image sensor 44, and the shield pipe 41 and the outer member 3 (the distal end cylindrical portion 31 and the cylindrical body 32) thermally expand, the thermal expansion of the outer member 3 is larger than that of the shield pipe 41, and the close contact between the shield pipe 41 and the outer member 3 can be prevented. As a result, it is possible to prevent heat from the image sensor 44 from being transferred to the outer member 3 via the shield pipe 41.

Furthermore, as described above, in the endoscope 1 according to the present embodiment, the thermal conductivity of the distal end cylindrical portion 31 exposed to the outside is lower than the thermal conductivity of the cylindrical body 32 that is not exposed. Therefore, even in a case where heat from the image sensor 44 is transferred to the outer member 3 via the shield pipe 41, it is possible to prevent high heat from being transferred to the skin of the patient via the distal end cylindrical portion 31.

As illustrated in FIG. 2, the outer peripheral surface of the outer member 3 is covered with the cover tube 26. That is, the cover tube 26 is externally fitted to the outer member 3. As described above, the outer peripheral surface of the one end portion of the distal end cylindrical portion 31 is surrounded by the cover tube 26, and the entire outer peripheral surface of the cylindrical body 32 is surrounded by the cover tube 26.

The cover tube 26 is made of a material with excellent heat insulating properties. Specifically, the cover tube 26 is made of a material with a lower thermal conductivity than the distal end cylindrical portion 31. For example, the cover tube 26 is made of fluororubber.

As described above, the cover tube 26 covers the entire outer peripheral surface of the cylindrical body 32. Therefore, even in a case where heat from the image sensor 44 is transferred to the outer member 3 via the shield pipe 41 though the thermal conductivity of the cylindrical body 32 is higher than the thermal conductivity of the distal end cylindrical portion 31, it is possible to prevent high heat from being transferred to the skin of the patient.

In the above description, the case where the thermal conductivity of the cover tube 26 is 0.2 to 0.25 W/(m·K) has been described as an example, but it is not limited thereto.

Figure 5:
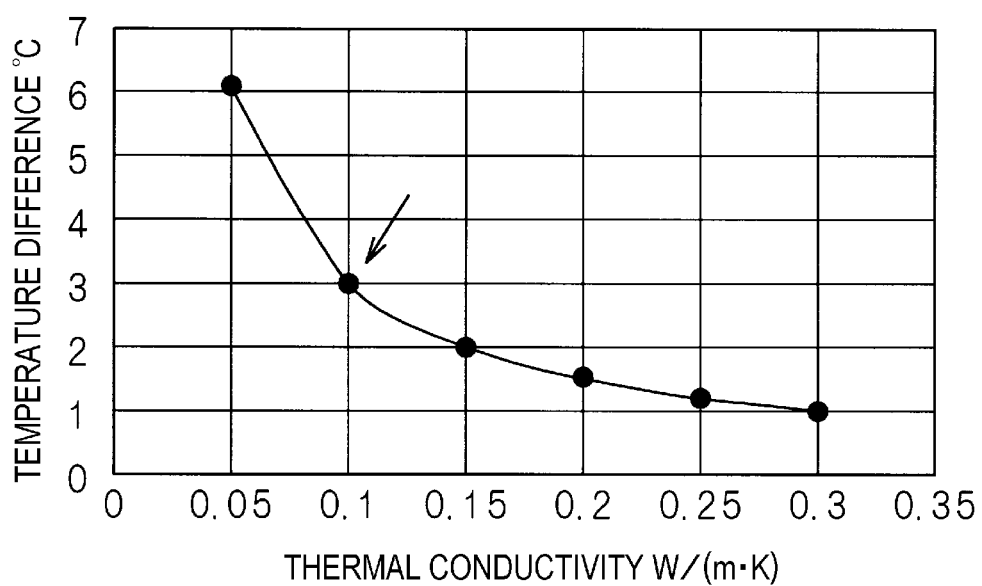
FIG. 5 is a graph showing a relationship between a thermal conductivity of a cover tube and a temperature difference between the inside and the outside of the cover tube.

FIG. 5 is a graph showing a relationship between a thermal conductivity of the cover tube 26 and a temperature difference between the inside and the outside of the cover tube 26. In FIG. 5, the horizontal axis represents the thermal conductivity of the cover tube 26, and the vertical axis represents the temperature difference between the inside and the outside of the cover tube 26. That is, FIG. 5 shows how much temperature difference is generated between the inside and the outside of the cover tube 26 depending on the thermal conductivity of the material of the cover tube 26. Here, FIG. 5 shows a calculation result on the assumption that the thickness of the cover tube 26 is 0.5 mm, the outer diameter of the endoscope 1 is 10.75 mm, and the power consumption of the image sensor 44 is 0.23 mW.

As can be seen from FIG. 5, the lower the thermal conductivity of the cover tube 26, the larger the temperature difference between the inside and the outside of the cover tube 26, and the lower the risk of burns. In particular, in a case where the thermal conductivity of the cover tube 26 is equal to or less than 0.1 W/(m·K) (see the arrow in FIG. 5), the temperature difference between the inside and the outside of the cover tube 26 rapidly increases. Therefore, by using a material with a thermal conductivity of 0.1 W/(m·K) or less as the material of the cover tube 26, the risk of burns can be effectively reduced.

In general, in view of the fact that the human body burns at 70° C. or higher and the guaranteed upper limit temperature of the image sensor 44 is 75° C., the temperature difference between the inside and the outside of the cover tube 26 is desirably equal to or more than 6° C. Therefore, by using a material with a thermal conductivity of 0.05 W/(m·K) or less as the material of the cover tube 26, the risk of burns can be reduced more reliably.

In the present embodiment, the case where the shield pipe 41 is made of nickel has been described as an example, but it is not limited thereto. The shield pipe 41 may be made of, for example, Al, SUS, Cu, brass, Ti, or Fe.

In the present embodiment, the case where the mold resin portion 48 is made of epoxy has been described as an example, but it is not limited thereto. The mold resin portion 48 may be made of, for example, a silicone-based resin, an acrylic-based resin, a urethane-based resin, a melamine-based resin, a hot-melt-based resin, or the like.

Modification

The case where the intervention member 45 is interposed between the shield pipe 41 and the mold resin portion 48 has been described above as an example, but it is not limited thereto, and the intervention member 45 may be omitted.

In such a modification, it is only required that the compression rate of the shield pipe 41 in a high temperature environment of 70 to 80° C. is equal to or more than 20%. The compression rate of the shield pipe 41 is obtained by Formula 1 described above.

In the formula, T1 is the thickness of the shield pipe 41 at room temperature, and T2 is the thickness of the shield pipe 41 in the high temperature environment.

In addition, as described above, since the linear expansion coefficient of the mold resin portion 48 is larger than the linear expansion coefficient of the shield pipe 41, in a case where thermal expansion occurs due to heat generation of the image sensor 44, the mold resin portion 48 and the shield pipe 41 can be brought into close contact with each other.

As described above, since the linear expansion coefficient of the mold resin portion 48 is larger than the linear expansion coefficient of the shield pipe 41, and the compression rate of the shield pipe 41 is equal to or more than 20%, heat generated from the image sensor 44 is quickly transferred to the shield pipe 41, and is effectively dissipated.

REFERENCE SIGNS LIST 1 endoscope
3 outer member
4 imaging assembly
26 cover tube (exterior member)
31 distal end cylindrical portion (first outer member)
32 cylindrical body (second outer member)
41 shield pipe (second heat dissipation member)
44 image sensor (heat generating portion)
45 intervention member
48 mold resin portion (first heat dissipation member)

The invention claimed is:

1. An endoscope comprising:
an image sensor that generates heat during operation; and
a heat dissipation shield that dissipates heat transferred from the image sensor, wherein
the heat dissipation shield includes a mold resin sheet that covers the image sensor and a cylindrical shield pipe with a cylindrical shape in which the mold resin sheet is internally fitted, and
the mold resin sheet has a linear expansion coefficient larger than linear expansion coefficients of the image sensor and the cylindrical shield pipe.

2. The endoscope according to claim 1, wherein
an intervention sheet formed in a sheet shape is disposed between the mold resin sheet and the cylindrical shield pipe, and
a linear expansion coefficient of the intervention sheet is larger than linear expansion coefficients of the image sensor and the heat dissipation shield.

3. The endoscope according to claim 1, further comprising an outer cylinder in which the cylindrical shield pipe is internally fitted, wherein
the outer cylinder has a linear expansion coefficient larger than a linear expansion coefficient of the cylindrical shield pipe.

4. The endoscope according to claim 3, wherein
the outer cylinder includes a first outer cylinder exposed to outside and a second outer cylinder not exposed, and
the first outer cylinder has a thermal conductivity lower than a thermal conductivity of the second outer cylinder.

5. The endoscope according to claim 4 further comprising a cover tube with a circular tube shape in which the second outer cylinder with a cylindrical shape is internally fitted, wherein
a thermal conductivity of the cover tube is equal to or less than 0.1 W/(m·K).

6. The endoscope according to claim 5, wherein a thermal conductivity of the cover tube is equal to or less than 0.05 W/(m·K).

7. The endoscope according to claim 1, wherein
the mold resin sheet includes epoxy, and
the cylindrical shield pipe includes nickel.

8. The endoscope according to claim 1, wherein a compression rate of the cylindrical shield pipe is equal to or more than 20%.

9. The endoscope according to claim 2, wherein a compression rate of the intervention sheet is equal to or more than 20%.

* * * * *